(12) United States Patent
Dickens et al.

(10) Patent No.: US 6,398,859 B1
(45) Date of Patent: Jun. 4, 2002

(54) RESIN-BASED PULP CAPPING AND BASING CEMENTS

(75) Inventors: Sabine H. Dickens, Gaithersburg; Shozo Takagi, Gaithersburgh, both of MD (US)

(73) Assignee: American Dental Association Health Foundation, Gaithersburg, MD (US)

( * ) Notice: Subject to any disclaimer, the term of this patent is extended or adjusted under 35 U.S.C. 154(b) by 0 days.

(21) Appl. No.: 09/471,037

(22) Filed: Dec. 23, 1999

Related U.S. Application Data

(60) Provisional application No. 60/113,578, filed on Dec. 24, 1998.

(51) Int. Cl.[7] .................................................. A61K 6/06
(52) U.S. Cl. ........................ 106/35; 433/288.1; 523/116
(58) Field of Search ........................ 106/35; 433/288.1; 523/116

(56) References Cited

U.S. PATENT DOCUMENTS

| | | | |
|---|---|---|---|
| 4,684,673 A | 8/1987 | Adachi | 523/11 |
| 4,746,686 A | 5/1988 | Waller | 522/14 |
| 5,508,342 A | 4/1996 | Antonucci et al. | 524/788 |
| 5,614,175 A | 3/1997 | Winston et al. | 424/521 |
| 5,814,681 A | 9/1998 | Hino et al. | 523/113 |

FOREIGN PATENT DOCUMENTS

JP      2-250809      * 10/1990

OTHER PUBLICATIONS

Dickens–Venz et al, "Physical and Chemical Properties of Resin–reinforced Calcium Phosphate Cements", Dent. Mater., vol. 10, pp. 100–106, Mar. 1994.*
Translation for JP 02–250,809.*

D. Skrtic, E.D. Eanes and J. M. Antonucci, Industrial Biotechnological Polymers, "Polymeric Calcium Phosphate Composites With Remineralization Potential", Chapter 25, 1995, pps. 393–408.

Skritic D., Antonucci JM, Eanes ED, Improved Properties of Amorphous Calcium Phosphate Fillers in Remineralizing Resin Composites, *Dent Mater* 12:5, Sep. 1996.

Skrtic D., Hailer AW, Takagi S., Antonucci JM, Eanes ED, Quantitative Assessment of the Efficacy of Amorphous Calcium Phosphate/Methacrylate Composites in Remineralizing Caries–like Lesions Artifically Produced in Bovine Enamel, J Dent Res, 75:9, 1679–86, Sep. 1996.

G. M. Flaim, S.H. Dickens, T.L. Galloucis, S. Takagi, J Dent Res 78 (IADR Abstracts), In vitro Properties of Ca–PO$_4$ Resin Cements with Remineralization Potential, 1999, No. 434.

S. H. Dickens, G. M. Flaim, S. Takagi, H. Liao, J Dent Res 77 (AADR Abstracts), Remineralization of Dentin and Enamel Lesions with Calcium Phosphate Cements, 1998, No. 769.

Sabine H. Dickens–Venz, Shozo Takagi, Lawrence C. Chow, Rafael L. Bowen, Allen D. Johnston, Brian Dickens, Physical and Chemical Properties of Resin–Reinforced Calcium–Phosphate Cements, Mar. 1994, pps. 100–106.

* cited by examiner

*Primary Examiner*—C. Melissa Koslow
(74) *Attorney, Agent, or Firm*—Banner & Witcoff, Ltd.

(57) ABSTRACT

A pulp-capping and base/lining cement comprising the combination of paste 1 and either paste 2 or a powder, wherein paste 1 contains a carboxylated monomer, dicalcium phophate, and water; and paste 2 or the powder contains a polymerizable base monomer and tetracalcium phosphate. The cement is useful in the repair and/or restoration of dental lesions as well as repair and/or restoration of other calcium and calcium phosphorus containing parts of living organisms.

50 Claims, 4 Drawing Sheets

RESIN-BASED PULP CAPPING AND BASING CEMENTS

Benefit of the Dec. 24, 1998 filing date of the provisional application Ser. No. 60/113,578 by the same inventors and entitled "Resin-Based Pulp Capping And Basing Cement" is hereby claimed and incorporated by reference in its entirety.

FIELD OF THE INVENTION

The invention relates to a composition useful in the repair and/or restoration of dental lesions as well as repair and/or restoration of other calcium and calcium phosphorus containing parts of living organisms.

BACKGROUND OF THE INVENTION

Remineralization of dentin enamel and bone utilizing calcium phosphate materials has been the subject material of intense experimentation and research. Nonetheless, there has remained a need for improved remineralization techniques and materials.

Dental cements are materials traditionally used under permanent restorations and, with the exception of polycarboxylate and glass ionomer cements, do not adhere to tooth structure. Their function and effectiveness lies mainly in insulation of the living tooth tissue (the pulp and the dentin) against thermal and bacterial effects from the oral cavity. While many of these materials have thus been effective base cements, they can do little to promote any healing effects to the diseased tooth tissues.

Other cements, so-called pulp-capping materials, promote the repair mechanism of dentin in the case of a perforated pulp. However, these materials have low strength and do not adhere to dentinal tissue. Clinically, the failure of pulp capping is directly related to the inability of $Ca(OH)_2$, for example, to provide a long-term seal against microleakage.

Newer technology has led to the development of a number of cement-type materials with various desirable properties, e.g., biocompatibility; ease of use due to the ability of being cured on command with light-curing; and higher strength; as for instance, in resin-reinforced glass ionomer cements. Many materials used today lack at least one of these properties, leaving the dentist with less than optimal choices for the caries treatment. There is a need for a strong material that serves not only as a base and pulp-capping material, but will also induce reparative mechanisms of carious dentin and/or enamel.

None of the cements that are currently in use can act in this dual manner as a pulp-capping/basing cement while simultaneously promoting the repair of mineral deficient tooth structure through the precipitation of tooth-like minerals.

For example, Antonucci et al., U.S. Pat. No. 4,832,745, describes a polymeric amorphous calcium phosphate composition to be used as a mineralizing composition for skeletal tissue, which contains a mixture of an unsaturated monomer systems and a particulate mineralizing agent. The composition contains approximately 40% amorphous calcium phosphate (ACP) mixed with approximately 60% monomers. While the ACP-based formulation has a reasonable potential for mineralizing carious enamel (no data on dentin remineralization have been provided), the monomer formulation cannot adhesively bond to hard tooth tissue nor does it contain or would be able to release any fluoride.

Since Antonucci's invention contains 40% calcium phosphate minerals, such cement consists mostly of resin. High organic fraction resins typically do not provide the necessary strength required from a base cement. Also, a cement of such composition may not be suited as a base cement, since the coefficient of thermal expansion due to the high organic mass, is considerably high.

Hino et al., U.S. Pat. No. 5,814,681, describes a restorative composition for hard tissue containing calcium phosphates and polymerizable monomers. Each paste contains calcium phosphates as fillers and a monomer mixture comprised of 2 monomers, one of which is a mono-, di-, or tri-ethyleneglycol dimethacrylate or polypropyleneglycol dimethacrylate, (monomer of formula (1)). The second monomer (monomer of formula (2)) is an ethoxylated bisphenol A dimethacrylate. Hino claims that the restorative composition can be used as a bone cement, as well as a filler for the defect part of the bone, a bone prosthesis, or an artificial bone. However, Hino's composition would not provide adhesive properties.

Hino discloses that the combination of monomers (1) and (2) contains 40–65% by weight monomer of formula (1) and that the inorganic content of pastes A and B should be 75–85% by weight. Hino's use of calcium phosphates requires silanization treatment with methacryloxypropyltrimeth(eth)oxysilane. Although Hino mentions the use of secondary calcium phosphate and tetracalcium phosphate, the temperature used in the disclosed heat treatment to silanate the calcium phosphate fillers, would in the case of secondary calcium phosphate lead to the formation of pyrophosphate. Pyrophosphates are known to inhibit the formation of hydroxyapatite and would therefore be contraindicated for use as bone filling repair material where bone in growth is required to ultimately heal the defect. Also, Hino's use of hydroxyapatite powder as fillers would lead to a minimal release of calcium ions.

The cement formulation described by Waller, U.S. Pat. No. 4,746,686, for a visible light-activated hydroxyapatite-containing cavity liner is capable of leaching fluoride ions and contains a small proportion of a hydrophilic monomer. Apart from using hydroxyapatite as fillers, the cement mixture reported by Waller has a considerably low strength and a neutral pH.

Wang, U.S. Pat. No. 4,813,876 describes a cavity liner, that is photo-polymerizable and is based on calcium hydroxide. Walton, U.S. Pat. No. 4,886,843 describes a very similar composition containing calcium hydroxide or their precursors and ethylenically unsaturated, polymerizable compounds having a salicylate group. The latter two patents describe resin-based cements that could be used for pulp-capping; however, the calcium hydroxide-based cements lack a phosphate component and therefore would not lead to any remineralization.

A great number of highly biocompatible cements using calcium phosphates as fillers have been described. (Brown et al., U.S. Pat. Nos. 4,612,053; 4,518,430; RE33,221; Chow et al., U.S. Pat. No. 5,695,729; Winston et al., U.S. Pat. Nos. 5,603,922; 5,833,957; 5,614,175; 5,817,296; Ison, U.S. Pat. Nos. 5,846,312; 5,496,399; Constantz, U.S. Pat. Nos. 5,129,905; 5,782,971; Imura et al., U.S. Pat. Nos. 5,569,490 and 5,652,016.) The majority are water based cements. Brown and Chow describe use of fillers in water-based self setting calcium phosphate cements consisting of tetracalcium phosphate (TTCP) and dicalcium phosphate anhydrate or dihydrate. The TTCP must have a Ca to P ratio of 2 or less.

Other prior art water based cements with reinforcing additives lack the advantage of being light-cured or do not have readily available $PO_4$ ions, that in combination with Ca ions could lead to the formation of the biornimetic hydroxyapatite. Cements that incorporate hydroxyapatite or other calcium phosphate powders and (poly)carboxylic acids are described by Adachi, U.S. Pat. No. 4,684,673; Liu, U.S. Pat. No. 5,218,035 and Bajpai, U.S. Pat. No. 4,668,295. Jochum and Gasser, U.S. Pat. No. 4,542,172 describe a lining and pulp-capping mixture based on calcium hydroxide, salicylic acid esters and poly-vinylbutyral as a binder. Aoki et al., U.S. Pat. No. 4,452,167, describes a dental cement composition, comprising hydroxyapatite, and acrylic acid/itaconic acid copolymers as the hardener.

SUMMARY OF THE INVENTION

The invention is directed to a pulp-capping and base/lining cement formulation comprising the combination of two pastes or a liquid and a powder. Each paste contains a polymerizable monomer, a calcium phosphate powder, and other additives. The monomers provide an adhesive resin component and a reinforcing base resin component. The calcium phosphate powders are tetracalcium phosphate and dicalcium phosphate. A preferred embodiment provides a paste composed of a polymerizable base monomer and tetracalcium phosphate. Other additives include catalysts able to initiate polymerization of the resin components and a fluoride-releasing compound. After the two pastes or liquid and powder are combined, the cement contains dispersed in unsaturated monomers calcium phosphate fillers, which then form hydroxyapatite when exposed to moisture. The monomers will harden into a polymer network.

The hardened cement consists of hydroxyapatite, some residual non-apatitic calcium phosphates, and an organic matrix. The hydroxyapatite may be present in quantities of 0 to 100 wt %, typically between 10 and 75 wt %. During and after setting, the calcium phosphate resin cement has a basic pit provides freely available calcium and phosphate ions, and provides slow and continuous release of fluoride. The cement also has adhesive properties, which is unique for a material that can be used for indirect or direct pulp-capping procedures.

The pulp-capping and base/lining cement formulation can be used for reconstruction of diseased or lost tooth structure or as a prophylactic treatment. Because of its high strength, the cement is useful as a basing material, and because of its adhesive properties, the cement will be able to seal the perforated pulp against bacterial invasion. In addition, it is believed that the cement will stimulate the formation of reparative dentin because of its basic pH during and after setting and will also promote remineralization of mineral deficient tissues.

The invention is directed to a two-part resin composition. When the two parts are combined, a mixture results of an acidic resin, tetra calcium phosphate powder, dicalcium phosphate powder, and water to provide two interpenetrating, reacting phases—a polymeric phase and a mineral phase. The pH of the mixture when initially mixed is at least about 11, but after about 24 hours, the pH of the mixture is about 8 to 12, preferably about 8 to 11, more preferably about 10. The higher pH allows the reacted mixture to be utilized for dental repair.

The invention is also directed to a method of dental repair comprising applying the rapidly curing mixture as a tooth repair or filling material to provide adequate strength and properties which stimulate natural regenerative repair of the damaged pulped region.

Numerous other features, objects and advantages of the invention will become apparent from the following detailed description.

DETAILED DESCRIPTION OF THE INVENTION

Figure 1:
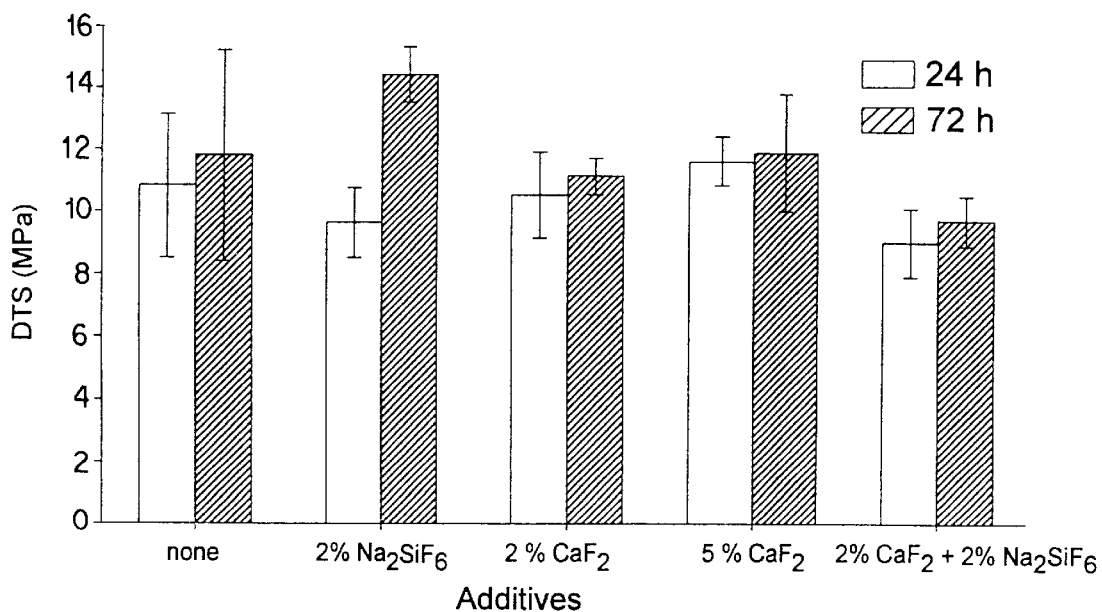
FIG. 1 depicts the diametial tensile strength of cements without and with additives after storage in water for 24 h and 72 h.

Good dental practice uses liners and basing materials prior to application of a number of restorative materials to protect the pulp from thermal and chemical irritation. Initially, it was assumed that pulpal inflammation was caused by toxins from dental materials. It is now believed that adverse pulpal reactions are primarily caused by bacterial activity and their toxins.

Many types of materials have been used in the treatment of the exposed pulp. In such treatments, it is most important to seal the pulp and prevent bacterial invasion. A pulp capping material with a high pH will cause mummification and cauterization of the bleeding pulp, followed by necrosis and initiation of a repair process. Such high pH material may further assist in the formation of reparative dentin, because of its antibacterial properties.

The repair process, which is carried out by the remaining vital tissue in the pulp, results in cell growth, cell differentiation, the formation of collagen in the wound area, and bridging of the defect by the formation of reparative dentin. A material with a pH approaching 12 will induce this repair process, but the initial effect of the high pH agent is considerable chemical injury of the pulpal tissue. Therefore, materials with a somewhat lower pH of about 10 are preferred. A material in this pH range will cause less extensive injury to the pulpal tissue than higher pH materials, yet provide enough stimulation to initiate the formation of reparative dentin. Moreover, as it has been shown that exposed dental pulps possess inherent healing potential, when they are adequately sealed against bacterial invasion, thus an ultra-high pH in a pulp-capping material may not be necessary for a successful pulp capping procedure.

The instant invention is directed to a calcium phosphate resin cement containing tetracalcium and dicalcium phosphates, a carboxylated monomer, and a polymerizable base monomer, as a pulp-capping and base/lining cement. The hardened cement consists of hydroxyapatite, some residual tetracalcium and dicalcium phosphates, and an organic polymeric matrix. The calcium phosphate resin cement has a basic PH freely available calcium and phosphate ions, and has adhesive properties, all important factors for a material that can be used for indirect or direct pulp-capping procedure.

The calcium phosphates employed as the solid phase in the calcium phosphate resin cement are those used in a self-setting bone cement. The bone cement is prepared from water and an equimolar mixture of tetracalcium phosphate and dicalcium phosphate anhydrous, which react to form the less soluble hydroxyapatite as the only product when the stoichiometry is in accordance with equation (1). The reaction is driven by the solubility characteristics of the components.

$$2Ca_4(PO_4)_2O + 2CaHPO_4 \rightarrow (Ca_{10}(PO_4)_6(OH)_2) \quad (1)$$

Combining calcium phosphate cements with carboxylated monomers results in a material comprised of calcium phosphate crystallites surrounded by a polymer. This material combines the high biocompatibility of hydroxyapatite with soft and hard tissues with the improved handling and setting characteristics conveyed by the resinous component. The resin component also provides the handling characteristics and strength necessary for using this cement clinically as a direct and indirect pulp capping agent that can support overlying permanent restorative materials.

The composition has a basic pH that develops when the freshly mixed cement is adapted on a perforated pulp. Such high pH assists in cauterization of the bleeding pulp, thereby avoiding leakage from underneath the pulp coverage. The high pH is further of advantage as it has a bactericidal to bacteriostatic effect.

The pulp-capping and base/lining cement can be prepared as a powder/liquid formulation (composition shown in the table) or comprises the combination of two pastes, paste 1 and paste 2.

|  | Cement A | Cement B |
| --- | --- | --- |
| EBPADMA | 7.6 | 7.6 |
| PMGDM | 7.4 | 7.4 |
| water | 9.9 | 9.9 |
| $TTCP_{2.05}$ | 56.3 | 55.2 |
| DCPA | 18.3 | 17.9 |
| $Na_2SiF_6$ | — | 1.5 |
| $CaF_2$ | — | — |
| CQ | 0.08 | 0.08 |
| DMAPE | 0.10 | 0.10 |
| BPO | 0.4 | 0.4 |

EBPADMA=ethoxylated bisphenol A dimethacrylate; PMGDM=pyromellitic glycerol dimethacrylate; $TTCP_{2.05}$=calcium-enriched tetracalcium phophate; DCPA=dicalcium phosphate; $Na_2SiF_6$=sodium hexafluorosilicate; $CaF_2$=calcium fluoride; CQ=camphorquinone; DMAPE=N,N-dimethylamino phenethanol; BPO=benzoyl peroxide.

Paste 1 contains a carboxylated monomer, dicalcium phosphate, and water. The carboxylated monomer may be any carboxylated monomer that provides the adhesive resin component. Generally, the carboxylate is a polymerizable compound with one or more carboxylic acid groups. Carboxylate monomers include all polymerizable carboxylic acid containing monomers including, but not limited to pyromellitic glycerol dimethacrylate (PMGDM),

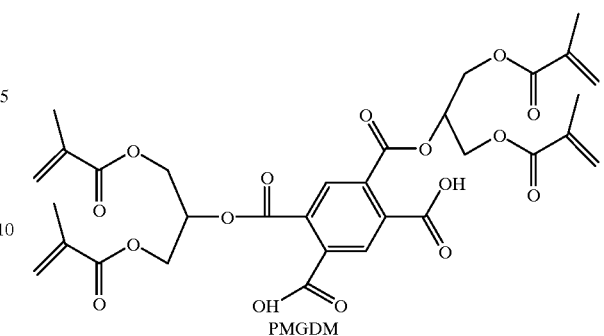
PMGDM 5-(2,5-dioxyl tetrahydrofuranyl)-3-methyl-3-cyclohexene-1,2-dicarboxylic anhydride bis(glycerol dimethacrylate) adduct. The chemical structure if one of four possible isomers is shown below.

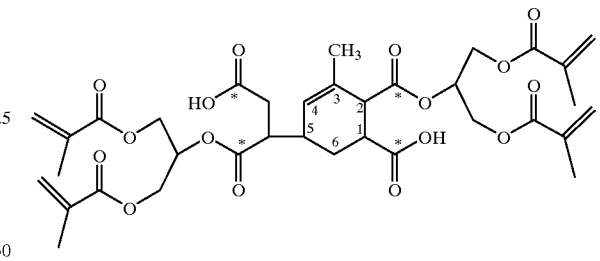

Each GDM can be attached to either of the two carbon atoms marked by an asterisk, in the original acid anhydride group.

Biphenyltetracarboxylic dianhydride—glycerol dimethacrylate (BPGDM). The structure of one of the four isomers is shown below.

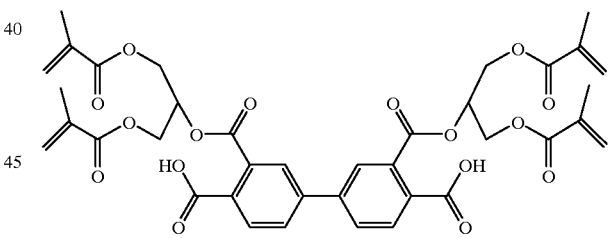

The adducts of pyromellitic glycerol dimethacrylate and hydroxybutyl (propyl) methacrylate and the adduct of phthalic anhydride and glycerol dimethacrylate.

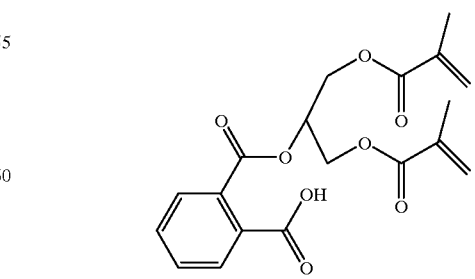

Preferably the carboxylate monomer is pyromellitic glycerol dimethacrylate.

Paste 1 may also contain a fluoride source such as, but not limited to, sodium hexafluoro silicate, calcium fluoride, and mixtures thereof, a photoinitiator such as, but not limited to, camphorquinone; and/or a catalyst such as, but not limited to, benzoyl peroxide. Suitable flouride sources, photoinitiators, and catalysts are known to those of skill in the art.

Paste 2 contains a polymerizable base monomer and tetracalcium phosphate. Preferably, the tetracalcium phosphate has a Ca to P mole ratio of 2.0 to 2.1, preferably 2.05. The polymerizable base monomer may be any base monomer that provides the reinforcing base resin component. Generally, the base monomer is a a monomer of suitable viscosity to provide sufficient strength to the forming polymer network. Suitable monomers include, but are not limited to, ethoxylated bis phenol A dimethacrylate, bisphenol A bis(glycidyl methacrylate) also know as Bis-GMA and urethane dimethacrylate. Preferably the base monomer is ethoxylated bis phenol A dimethacrylate.

Paste 2 may also contain a coinitiator such as, but not limited to, N,N-dimethylaminophenethenol or any other suitable tertiary amine coinitiator.

Other additives may be added to pastes 1 and 2 as well known to those skilled in the art butylated hydroxytoluene or other stabilizers to prevent radical formation and premature polymerization of the monomers.

When the pastes are combined, the cement formulation contains as its liquid a mixture of water, pyromellitic glycerol dimethacrylate (PMGDM or other carboxylated monomer and ethoxylated bis phenol A dimethacrylate (EBPADMA) or other polymerizable base monomer.

Paste 1 preferably contains about 20 to about 60 wt % dicalcium phosphate, preferably about 48 wt %, and about 10 to about 40 wt % carboxylated monomer, preferably about 20 wt %. Paste 2 preferably contains about 50 to about 90 wt % tetracalcium phosphate, preferably about 88%, and about 10 to about 40 wt % polymerizable base monomer, preferably about 12 wt %.

The pastes are formulated so that the resulting mixture will contain an overall calcium phosphate concentration of about 40 to about 80 wt %, preferably about 40 to about 74 wt %, more preferably about 73 wt %, whereby about 60 to about 80 wt %, is tetracalcium phosphate, preferably about 76 wt %, and about 20 to about 40 wt % is dicalcium phosphate, preferably about 24 wt %.

In paste 1 the fluoride source is present in an amount of about 0.5 to about 8 wt %, preferably about 4 wt %. The photoinitiator is present in an amount of about 0.05 to about 5 wt %, preferably about 0.2 wt %. The catalyst is present in an amount of about 0.5 to about 10 wt %, preferably about 1 wt %. Water is present in an amount of about 5 to about 40 wt %, preferably about 2.5 to about 27 wt %.

In paste 2, the coinitiator is present in an amount of about 0.05 to about 2 wt %, preferably about 0.2 wt %.

The pastes react with each other and may form hydroxyapatite when mixed in the correct proportions. After mixing a rise in pH occurs.

A silanization procedure, such as described in Hino, is not required because of the use of the carboxylated monomer which can form ionic bonds to the calcium phosphates used and which also promotes adhesion to dental hard tissues. In fact silanization of the calcium phosphates could delay and possibly prevent the formation of hydroxyapatite.

The combination of a high, bactericidal (bacteriostatic) pH, adhesion to dentin of materials placed on the perforated pulp is important to the long-term success of the pulp capping procedure. The latter is effected by preventing bacterial invasion of the pulp chamber as a consequence of the capping agent forming a tight seal against exterior noxes and by the formation of secondary dentin.

The tetracalcium phosphate (TTCP) may be regular TTCP having a Ca/P ratio of 2 or lower. In this case, a small amount, e.g. 0.1 to 10 wt % CaO may be added to the cement mixture. It is preferred that a higher amount of calcium carbonate than stoichiometrically equivalent be used when preparing the TTCP resulting in a TTCP with residual CaO and a Ca/P ratio of 2.05. This material is abbreviated as $TTCP_{2.05}$, is termed "calcium-enriched TTCP".

In a preferred embodiment when the two pastes are combined, the cement comprises about 56 wt % $TTCP_{2.05}$ and about 18 wt % dicalcium phosphate anhydrous (DCPA), about 7.5 wt % pyromellitic glycerol dimethacrylate (PMGDM), about 7.5 wt % ethoxylated bisphenol A dimethacrylate (EBPADMA) and about 10 wt % water. The cement has an initial pH greater than 10 and a residual pH level of 9 to 10 after 20 h, which is the range commonly found in pulp-capping agents known to stimulate the formation of reparative dentin. Since the main purpose of the high pH is mummification and cauterization of the bleeding pulp, the initial high pH of this cement that occurs during the first hour after mixing is beneficial. The cement has higher strength compared to water-based calcium phosphate cements and is thus suitable as a pulp-capping and lining material when placed under more durable permanent restorative materials.

The adhesive resin used as part of the organic phase of the cement enhances its functionality as a pulp-capping material by improving the seal of the pulp against bacterial invasion. Since the resin has a retarding effect on the conversion of the calcium phosphate components to hydroxyapatite, initially Ca and $PO_4$ ions may be freely released from the light-cured cement and can, in theory, form a mineral deposit in mineral deficient tooth hard tissue.

Stimulating remineralization of mineral-depleted (carious) hard tooth tissues is an important material property. There is general agreement that the chemical processes leading to caries comprise the production of acids by bacteria and the dissolution and to some extent reprecipitation of tooth mineral. The release of fluoride from dental medicaments or materials is aimed at preventing or inhibiting recurrent caries. The protective mechanism from fluoride include a reduction in dissolution, by forming less soluble fluor- or fluorhydroxyapatite and the formation of $CaF_2$. In vitro models have shown that fluoride leached from glass ionomer cements and other fluoride enriched materials and/or mouthrinses has an inhibitory effect on artificially induced caries. By adding fluoride to the calcium phosphate cement the remineralization on artificial enamel and dentin lesions by the cement is further increased.

EXAMPLES

Example 1
Composition and Physical Properties of the Cariostatic Cement

A calcium phosphate resin cement was prepared by hand mixing calcium phosphate powder mixture with a resin system and water using 75% of the powder, 15% of the resin, and 10% water. The resin system consisted of 50% PMGDM and 50% EBPADMA, and was activated with 0.69% N,N-dimethylaminophenethanol (DMAPE), and 0.5% camphorquinone (CQ), a photoinitiator system enabling the calcium phosphate resin cement to be surface-cured with a visible light source (MAX, L. D. Caulk/Dentsply, Milford, Del., USA).

The filler mixture consisted of 75.5% $TTCP_{2.05}$ and 24.5% DCPA. This ratio resulted in a formulation having slightly more $TTCP_{2.05}$ than the equimolar mixture to compensate for the acidity of the resin component.

Various fluoride releasing additives were incorporated into the filler mixture shown above by mixing the powders with a blender. Sodium hexafluorosilicate ($Na_2SiF_6$) and calcium fluoride ($CaF_2$) were used as additives. The cements were designated Cement A: no fluoride additive; Cement B: 2% $Na_2SiF_6$; Cement C: 2 % $CaF_2$; Cement D: 5% $CaF_2$; and Cement E: 2% $CaF_2$+2% $Na_2SiF_6$. A catalyst, 0.5 % benzoyl peroxide (BPO), was also crushed into the filler mixture prior to mixing with the resin and water to ensure cure throughout the specimen.

Calcium phosphate resin cement specimens having the four filler compositions were prepared for diametral tensile strength (DTS) tests and fluoride release analyses. Specimens for the DTS test were stored in water at 37° C. for 24 h or 72 h respectively. The effects of incorporating the various fluoride releasing additives to the filler mixture of 75.5% $TTCP_{2.05}$ and 24.5% DCPA used in the Ca—$PO_4$ resin cements are depicted in FIG. 1. In all situations, measuring the DTS after 72 h resulted in higher values than measuring it after 24 h. The DTS of the cement that contained 2% $Na_2SiF_6$ was the highest of the four experimental cements. The DTS of this cement was (14.4±0.9) MPa (n=5), which is not significantly different (t-test; p>0.05) from that of the control, which was (11.8±3.4) MPa. Although the addition of 2% $Na_2SiF_6$ did not significantly increase the DTS of the calcium phosphate resin cement, it did not decrease it. However, the DTS of the other three experimental cements appeared to be equal or lower to that of the control.

Figure 2:
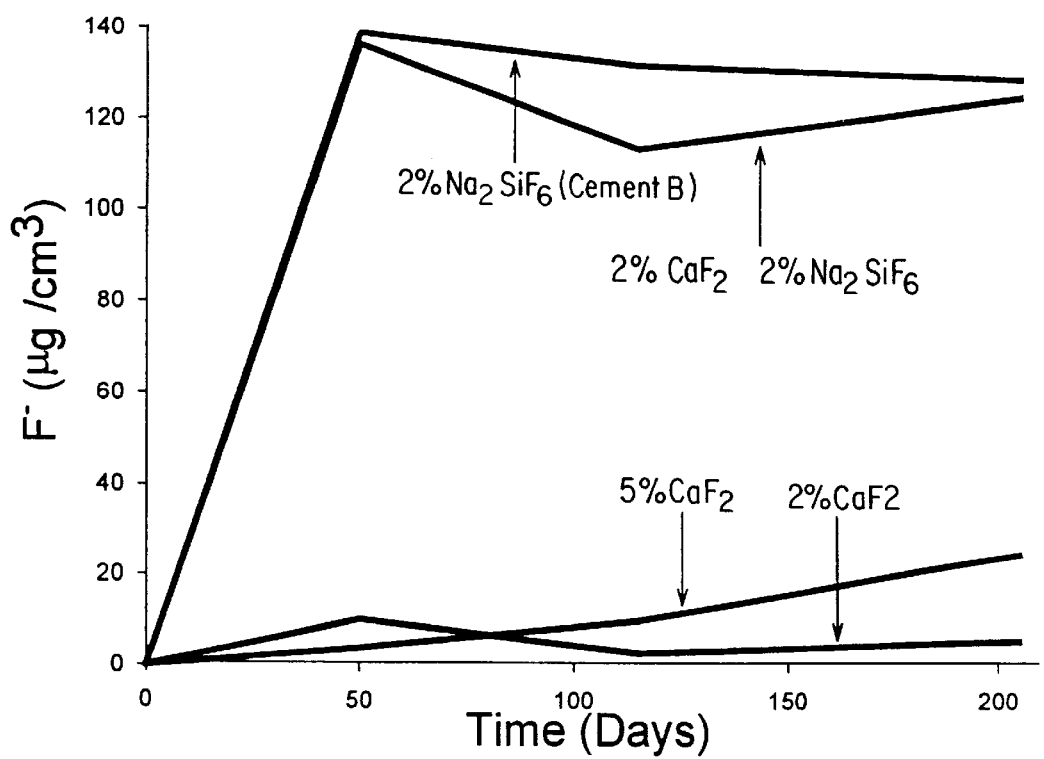
FIG. 2 depicts cumulative $F^-$ release from cements with various additives.

The total fluoride release in distilled water data for the four experimental cements containing the various fluoride additives are presented in FIG. 2. This figure indicates that the two cements having 2% $Na_2SiF_6$ release a substantially greater amount of fluoride than cements with only $CaF_2$. For the $Na_2SiF_6$-containing cements, there is a high initial fluoride release, which slowly levels off with time. The total fluoride released in distilled water after seven months for the cement with only 2% $Na_2SiF_6$ was 130±46 (g $F^-/cm^3$ (n=5). The two experimental cements containing $CaF_2$ released only a small amount of fluoride over the same seven-month period.

The cement containing 2% $Na_2SiF_6$ had a pH over the first 20 h after mixing of about 10. The high pH and a DTS of about 14 Mpa allows the material to serve as a pulp-capping agent and also as a lining or temporary filling material administered in situations that do not allow complete excavation of carious dentin. This cement released 2.3±0.3 mg/cm$^3$ of $Ca^{2+}$ (n=5) in 1 week and 130±46 (g/cm$^3$ of $F^-$ (n=5) in 7 months, suggesting that Ca, $PO_4$, and F ions are available to deposit mineral and remineralize enamel and dentin lesions. The amount of fluoride released from this cement is considerably below that released from conventional glass ionomer cements. However, the slow release of such low amounts of fluoride may may protect against carious attack and may promote the formation of fluoroapatite. Fluoride in sub-ppm concentrations may still be effective in promoting mineral deposition in demineralized tooth hard tissue and may be effective in inhibiting further mineral dissolution.

Example 2
Physical Properties of a Two-paste Cement

A calcium phosphate resin cement was prepared from mixing together two separate pastes. Paste 1 consisted of 48% DCPA, 4% $Na_2SiF_6$, 0.2% CQ, 1% BPO, 20% PMGDM, and 27% $H_2O$ and had a sticky consistency. Paste 2 was more of a powder; it consisted of 88% $TTCP_{2.05}$, 12% EBPADMA, and 0.2% DMAPE. To form the cement, 0.37 parts of Paste 1 and 0.63 parts of Paste 2 were hand mixed with a spatula. The resulting mixture contained 73% calcium phosphates, 1.5% sodium hexafluorosilicate, 10% water, 15% resin, and 0.6% initiators.

To prepare the cured test specimens, the mixture was inserted in molds, 6 mm in diameter and 3 mm high for the DTS test and 15 mm in diameter and 1 mm high for the biaxial flexure test, and light-cured for 1 min from each side. The DTS of the two-paste calcium phosphate resin cement was (36±2) MPa after 24 h in $H_2O$ at 37° C. In comparison, VLC Dycal had a DTS of (23±3) Mpa after 24 h and (14±2) Mpa after 4 weeks in water. The biaxial flexure strength of the Ca—$PO_4$ cement was (30±7) MPa after 48 h in $H_2O$ at 37° C. The biaxial flexure strength remained essentially unchanged after storage in water for 1 month (p>0.05). The pH of an aqueous slurry of the two-paste cement mixture over the first 24 h after mixing was about 9.

After two months storage in capped glass vials, the two pastes could still be used. Paste 1 was stored in a refrigerator while Paste 2 was stored in a dessiccator to prevent hydration. These properties exceed those of most cements used as bases for permanent restorations and demonstrate potential to be used as a supportive pulp capping composite.

Example 3
Adhesive Properties and Microleakage of the Calcium Phosphate Resin Cement A study was conducted to determine the dentin shear bond strength (SBS) and microleakage of the cement. Sixty teeth were sectioned horizontally through the crown exposing a flat dentin surface. For microleakage, preparations about 1.5 mm deep were cut into the dentin. In Group A, eight cavities were filled with the mixture of a two-paste cement consisting of the Ca—$PO_4$ components, resin and water. In Group B, eight cavities were etched with 37% $H_3PO_4$ for 15 s and rinsed prior to filling with the cement. The calcium phosphate resin cement restorations were light cured for 1 min.

In Group C, eight cavities were filled with Prisma VLC Dycal® (Dentsply/Caulk, Milford, Del.) according to manufacturer's instructions. The teeth were stored in water at 37° C. for 5 d, then thermocycled 2000 times at 5° C. to 55° C. The teeth were sealed within 1 mm of the margins of the restoration, stained with silver nitrate, and sectioned through the center of the restoration. The extent of staining was rated on each half on a scale of 0–4: 0=no staining; 1= up to ½ of the cavity depth; 2=entire cavity depth; 3=extending to ⅓ of the pulpal wall; 4=staining along the entire pulpal wall. For SBS with 12 teeth per group, metal irises were placed on the dentin and filled as described above.

After storage for 7 d in water at 37° C., shear bond strengths were tested at a crosshead speed of 0.5 mm/min. Kruskal-Wallis One Way ANOVA on ranks and Student-Neuman-Keuls post hoc tests were used at p<0.05. The median microloeakage scores were 1 and 2 for Groups A and B, respectively, and were significantly different from Group C, which had a median score of 4. The median SBSs were 3.7, 5.4, and 0.0 MPa in Groups A, B, and C, respectively. Groups A and B were significantly different from Group C. No differences were found for either test between the nonetched and the etched $Ca-PO_4$ resin cement treatments.

These results suggest that the resin component in the calcium phosphate cement mediated greater adhesion to dentin compared to the resin-containing calcium hydroxide cement Prisma VLC Dycal®.

Example 4
Remineralization of Artificially Demineralized Enamel and Dentin
Part I Preparation of teeth and microradiography. Single 120–140 $\mu$m thick sections of extracted human molars were cut and embedded in resin, leaving the dentin and buccal or lingual enamel surfaces exposed. Using a circular diamond saw, the crowns were first cut horizontally to remove the roots, then in a longitudinal direction parallel to the contact side of the teeth, so that the buccal and lingual enamel surfaces were preserved for testing. The thickness of the cut sections was approximately 150 $\mu$m. These sections were then ground by hand on wet sandpaper to a thickness of 120–140 $\mu$m. Next, the tooth sections were cut in half, and a nickel or copper grid commonly used for transmission electron microscopy (TEM), was attached about 250 $\mu$m–300 $\mu$m from the enamel and dentin edges of each half-tooth section with self-curing acrylic. Three sections for each treatment were then embedded in an acrylic resin having a thickness of approximately 0.5 mm. The edges were ground to expose the enamel and dentin, and then examined under a microscope to insure that they were exposed. The sections were immersed in 1 mL of a demineralizing solution for 22 h at 37° C. (static model). The demineralizing solution consisted of 0.075 mol/L glacial acetic acid, 0.002 mol/L Ca ($CaCl_2$), and 0.002 mol/L $PO_4$ ($KH_2PO_4$), and had a pH of about 4.3. The sections were then examined under a microscope to verify the formation of subsurface lesions. The exposed enamel surfaces or the exposed dentin surfaces were placed against a standard aluminum step wedge used to normalize the enamel and dentin mineral density, and contact microradiographs were taken.

Contact microradiographs of the tooth sections and the aluminum step wedge were obtained on Kodak SO0343 film exposed for 15 min to Ni-filtered $CuK_{60}$ radiation generated at 40 kV and 3 mA, and developed according to manufacturer's recommendations. The specimens were then placed on a glass slide and the Ca—PO4 resin cements were pressed against the exposed enamel or dentin surfaces. A second glass slide was placed on top, the two slides were pressed together and the cements were light cured for 1 min. Either $Ca-PO_4$ resin cement A (the $Ca-PO_4$ resin cement described in example 1 without a fluoride releasing additive) or $Ca-PO_4$ resin cement B (the $Ca-PO_4$ resin cement described in example 1 with 2% $Na_2SiF_6$) were used to remineralize the subsurface lesions. Cement B was chosen because it demonstrated the best combination of DTS and $F^-$ release, and Cement A was used as the control. The sections were placed in distilled water at 37° C. for 6 weeks. At the end of the 6 weeks, the cement was cut off the sections, and contact microradiographs were taken as was done before. All of the contact microradiographs were examined with a digital imaging program to assess the mineral content of the subsurface lesions and to establish if any re-deposition of mineral occurred.

Figure 3:
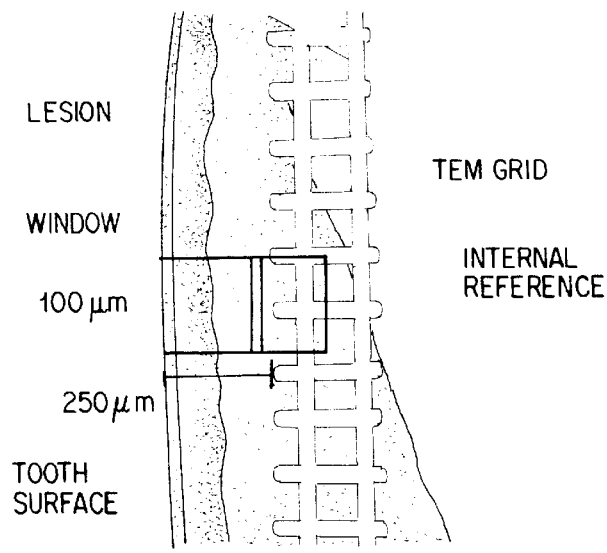
FIG. 3 depicts a digitized radiographic image of a partially demineralized enamel specimen showing a subsurface lesion.

Quantitative assessment of mineral content. The mineral content in the lesions before and after treatment was determined by quantitative analysis of the microradiographs using digital image analysis software interfaced with an optical microscope. The procedure consisted of the following steps 1) A standard calibration curve for each microradiograph was established by plotting the thickness of the Al step wedge vs. the average gray levels of the Al step wedge.
2) Three to four images of one tooth section before treatment were digitally captured. The images encompassed from left to right the edge of the enamel or dentin surface (vertically positioned near the left-hand boundary of the image), the subsurface lesion, the sound portion of the section, and the TEM grid (FIG. 3). Images of tooth sections after treatment were superimposed on the images of the tooth sections before treatment, and were then digitally captured.
3) For the internal reference of each sample, an area 100 $\mu$m high×(25–100) $\mu$m wide located in the sound portion of the enamel or dentin was chosen. The average gray levels of all the pixels located within this internal reference area were then converted to an average aluminum thickness through the use of the standard curve. This value represented a mineral content of 100%.
4) An area of about 100 $\mu$m high×426 $\mu$m wide was then measured. The area included the edge of the enamel or dentin surface, the subsurface lesion, the sound portion of the section, and the TEM grid. The measurements for a given area were processed by the computer averaging the gray levels of one column of pixels at a time. Each of the average gray levels were then further processed as follows.
5) The average gray levels were converted to aluminum thickness values as described above.
6) The average thickness values were then converted to % mineral content by ratioing them against the internal standard.
7) These data were used to produce a mineral content profile of the captured image as a function of distance from the enamel or dentin surface.

8) To obtain the amount of mineral loss in the lesion region, $\Delta Z$, the average % mineral content values were subtracted from 100%, which represented the sound portion of the enamel or dentin, and the sum of these values was then multiplied by the pixel width (1.326 $\mu$m). The lesion depth was taken as the point at which the mineral content was 95% of the sound portion of the mineral.

9) The $\Delta Z$ value after treatment was subtracted from the $\Delta Z$ value before treatment to obtain the change in mineral content, $\Delta(\Delta Z)$, in the lesion region that was due to the remineralizing cement that coated the lesion.

The results of the digital image analysis of microradiographs taken of human molar tooth sections before and after the sections were treated with either the control calcium phosphate resin cement A (without fluoride releasing additive) or calcium phosphate resin cement B (with 2% $Na_2SiF_6$) are summarized in Table 1.

The peaks in the mineral profiles close to the surface of the enamel specimens indicate that a "true" subsurface lesion was formed, as is demonstrated by having more mineral present close to the surface than within the body of the lesion.

TABLE 1

Mean and Standard Deviation of the changes in the mineral content in enamel and dentin after treatment with fluoride-free and fluoride-containing cement

|  | Enamel $\Delta(\Delta Z)$ in $\mu$m | Enamel % remineralization | Dentin $\Delta(\Delta Z)$ in $\mu$m | Dentin % remineralization |
|---|---|---|---|---|
| Cement A (fluoride-free) | 4.1 ± 3.3 (n = 9) | 8.9 ± 6.5 | -2.5 ± 4.3 (n = 9) | -3.5 ± 5.5 |
| Cement B (with fluoride) | 7.8 ± 4.6 (n = 9) | 14.3 ± 6.7 | 14.0 ± 5.3 (n = 9) | 14.6 ± 5.2 |

Table 1 contains the average $\Delta(\Delta Z)$ values for the two cements for both enamel and dentin. In order to be able to compare the results from parts I and II of this study, also shown in Table 1 is the remineralization in % expressing which fraction of the mineral lost in the demineralization process has been repaired by diffusion and reprecipitation from the calcium phosphate resin cements. The average values and standard deviations obtained from nine images (3 images on each of 3 sections) for each condition are reported.

Treatment of both enamel and dentin lesions with Cement B resulted in a significantly ($p<0.05$) greater amount of remineralization than treatment with Cement A Because the solubility product of fluoroapatite is lower than that of hydroxyapatite, crystal growth occurs more rapidly and less selectively. Thus, adding fluoride to the cement resulted in more mineral deposition, and thus more remineralization was confirmed. Treating dentin lesions with Cement A seemingly resulted in more demineralization, although it is suspected that the procedure of removing the cement from the specimen edges led to fractures, especially along the weaker dentin edges of those specimens that had been treated with the fluoride-free Cement A. Thus it is conceivable that the results for Cement A on dentin were obscured by an improper technique.

Part II

The extent of relative remineralization was determined on mid-coronal dentin of human molars. The minimal remineralization of dentin lesions in part I of the remineralization study was suspected to be caused by the preparation technique rather than a poor remineralization potential of the cement. Here, it was intended evaluate the remineralization potential with a more reliable technique than used previously and to study the remineralization induced by Cement B on artificial dentin lesions after incubating them in artificial saliva.

Figure 4:
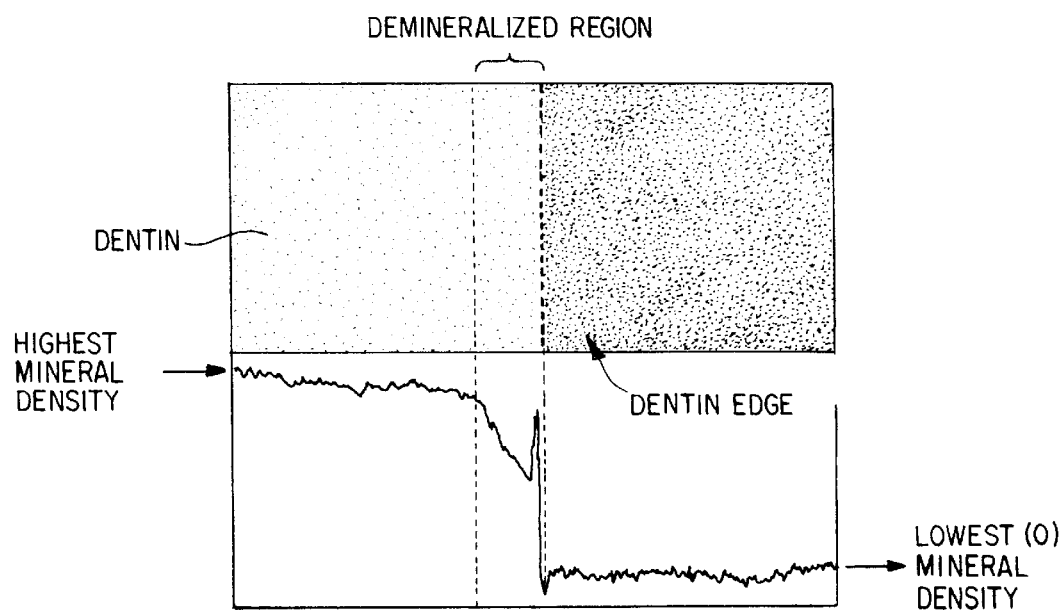
FIG. 4 depicts a mineral profile of demineralized dentin.

For this study, occlusal dentin surfaces were exposed to demineralizing solution for 48 h. A plastic disc with two bores was placed on the demineralized surface. The bores were filled with either a composite resin or Cement B, which were then light cured for 1 min. The teeth were incubated in artificial saliva at 37° C. for 5 weeks. Five 120 $\mu$m thick cross sections were cut. A digitized image from the area under Cement B and the composite resin and their corresponding mineral profiles were obtained. To obtain the profile, the computer program calculates the averages of the gray levels of one column of pixels at a time and plots them as a function of the distance from the left edge. This profile consists of 300 averaged points. The left side of the profile corresponds to the unaltered dentin, the right hand side to the background gray. The dip depicts an area of mineral deficient dentin. The spike corresponds to the white line on the dentin edge, adjacent to the background and is probably due to some residual cement attached to the dentin surface. The mineral density profiles of incubated dentin adjacent to composite resin and Cement B is depicted in FIG. 4. The extent of demineralization is depicted by an area enclosed between the two mineral profiles. The two mineral profiles were superimposed to graphically show the relative amount of remineralization. The quantitative results obtained from four teeth with an average of three sections per tooth are shown in the table in FIG. 4.

The overall remineralization was (54±16) %. The rather large difference in the amount of remineralization found between the two parts of the study may in part be explained by the environment in which the specimens were incubated. Because artificial saliva is saturated with respect to hydoxyapatite, less Ca and $PO_4$ will be dissolved in the surrounding medium and these ions are therefore available for deposition in the subsurface lesion. In conclusion: fluoride-releasing calcium phosphate cements were shown to remineralize artificial enamel and dentin lesions. The presence of fluoride potentiates the mineral deposition.

TABLE 2

The mean mineralization and their standard deviation (S.D.) from 3 specimens per tooth expressed as % of the originally demineralized areas.

| Tooth | 1 | 2 | 3 | 4 |
|---|---|---|---|---|
| Mean | 56 | 54 | 52 | 52 |
| S.D. | 19 | 4 | 15 | 26 |

Figure 5:
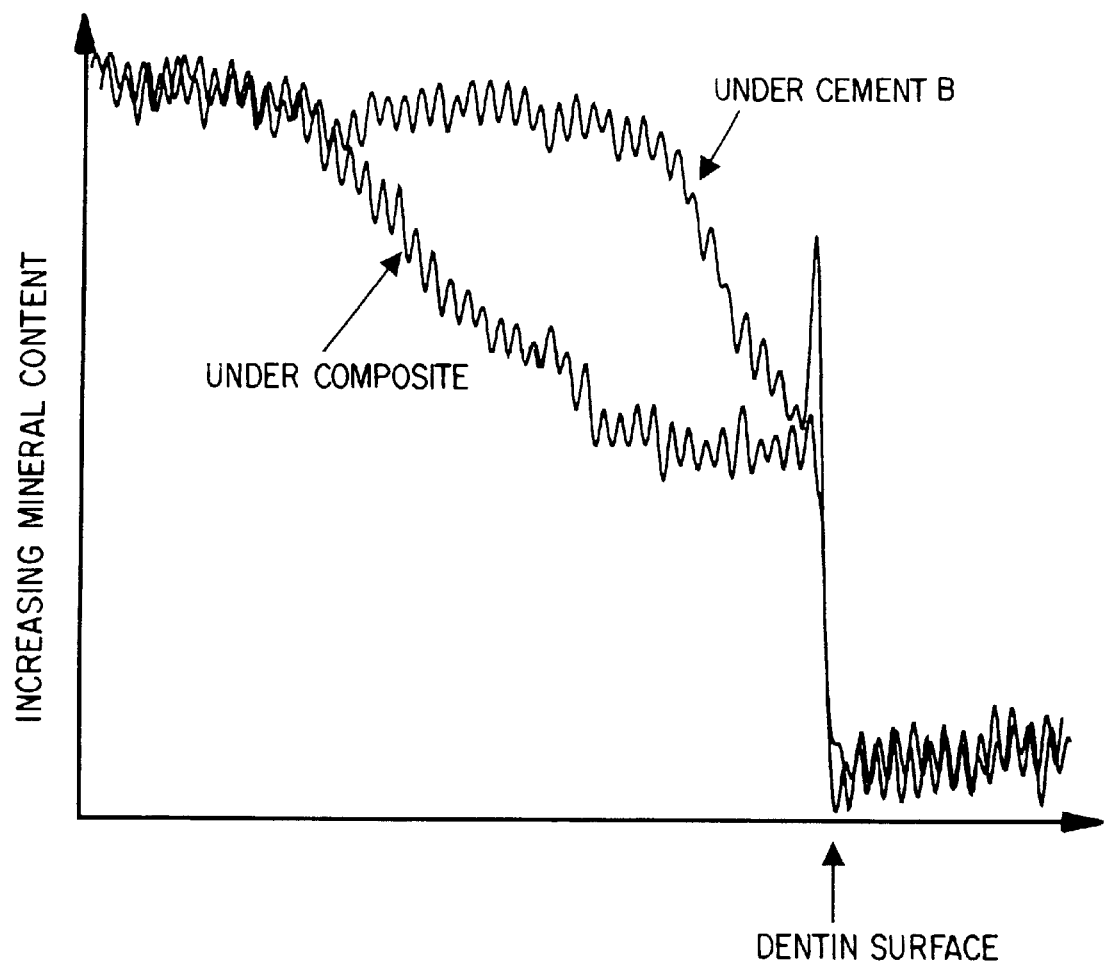
FIG. 5 depicts a mineral profile of the dentin surface under calcium phosphate cement B compared to the mineral profile under the composite resin.

The quantitative results obtained from the 4 teeth measured as shown in FIGS. 4 and 5 are displayed in Table 2. The overall remineralization was (54±16) %.

Figure 6:
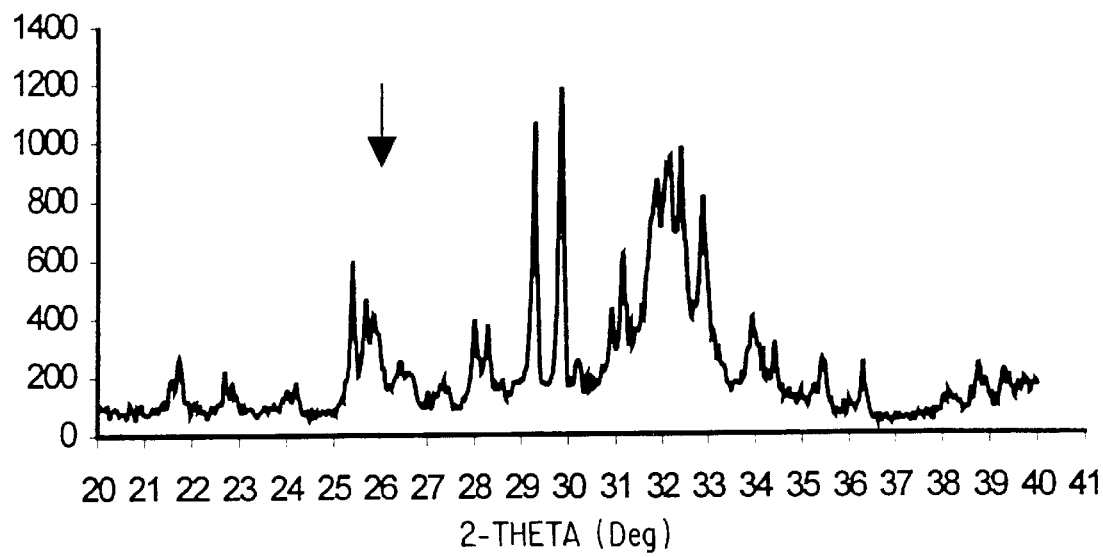
FIG. 6 depicts an X-ray diffraction pattern of the two-paste cement after various storage times in water.
Figure 6A:
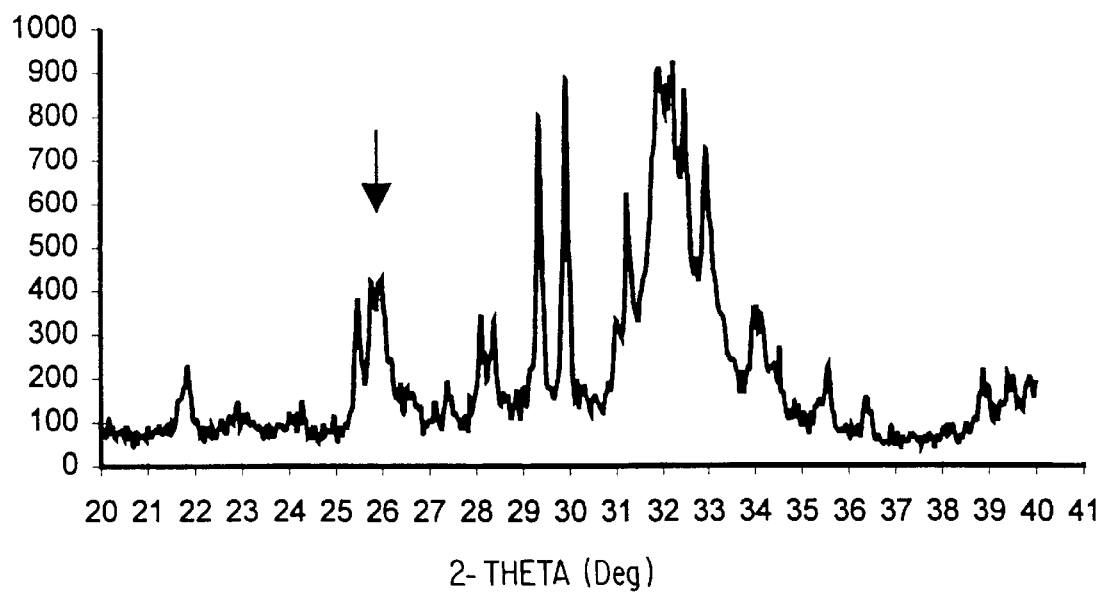

The formation of hydroxyapatite in the two-paste cement after 32 days and 7 months in water is displayed in FIG. 6. It is clearly shown that hydroxyapatite continues to form over a long time period. It can be expected that the continued conversion of the calcium phosphates to hydroxyapatite will aid in maintaining good strength of the cement and will also provide continued supply of Ca and $PO_4$ ions to the surrounding tooth tissues.

Example 5
Effect of $H_2O$ Concentrations on Physical Properties of Ca—$PO_4$ Resin Cements

| % water in Paste 1 | DTS after 24 h mean (sd) | DTS after 4 weeks mean (sd) |
|---|---|---|
| 2.9 | 41 (4) | 30 (2) |
| 6.95 | 42 (2) | 21 (4) |
| 8.82 | 40 (2) | 21 (2) |
| 10.33 | 36 (5) | 18 (2) |
| 14.82 | 30 (3) | 17 (3) |

This study was directed to paste 1 having a water content of about 3 wt % to about 15 wt %. A fluoride (F) releasing Ca—$PO_4$ resin cement (F-CPC) has been shown to remineralize artificial dentin and enamel lesions. This study determined the effect of varying the $H_2O$ concentration in a two paste system of the F-CPC on the in vitro properties: diametral tensile strength (DTS), biaxial flexure strength (BFS), hydroxyapatite (HA) formation, (F) release, and calcium (Ca) release. The nine components comprising the F-CPC were combined into two pastes, which upon mixing formed the light and chemical curing F-CPC. Five compositions of Paste 1 were made by varying the $H_2O$ concentration. The overall percentage of $H_2O$ in the set cements 1 through 5 was 1.1, 2.6, 3.3, 3.9, and 5.5, respectively. The composition of Paste 2 remained constant. For the DTS test, disks (6×3 mm) were made by light curing the cements for 1 min from each side. For the BFS test and the HA analysis the disks were 14 mm×1.5 mm. Similar disks were used for measuring F and Ca release in saliva-like solution. DTS and BFS specimens were tested after 24 h and 4 week $H_2O$ storage. BFS specimens were also examined by powder X-ray diffraction analysis to determine the amount of bulk and surface HA. The mean strengths in MPa for the two storage times were: DTS-41,30; 42,21; 40,21; 36,18; 30,17, and BFS- 69,51; 69,37; 68,36; 56,36; 51,39.

Two-way ANOVA of both strength tests showed significant effects of the two factors, $H_2O$ content and storage time ($p<0.001$). There was a significant interaction between the two factors with higher $H_2O$ and longer storage resulting in lower strength ($p<0.005$). About 20 to 30% HA formed in bulk and about 50% on the surface. Cumulative F release for groups 1 to 5 ranging from (590 to 250) μg/cc was inversely correlated to the increasing water content ($R^2=0.73$), while the cumulative Ca release for groups 1 to 5 ranging from (1500 to 3200) μg/cc showed a weak positive trend ($R^2=0.4$).

It will be apparent to those skilled in the art that various modifications and variations can be made in the compositions and methods of the present invention without departing from the spirit or scope of the invention. Thus, it is intended that the present invention cover the modifications and variations of this invention provided they come within the scope of the appended claims and their equivalents.

What is claimed is:

1. A pulp-capping and base/lining cement comprising the combination of paste 1 and paste 2, wherein paste 1 comprises a carboxylated monomer, dicalcium phosphate, a fluoride source and water; and paste 2 comprises a polymerizable base monomer and tetracalcium phosphate.

2. The cement of claim 1 wherein the carboxylated monomer is pyromellitic glycerol dimethacrylate; 5-(2,5-dioxyl tetrahydrofuranyl)-3-methyl-3-cyclohexene-1,2-dicarboxylic anhydride bis(glycerol dimethacrylate) adduct; biphenyltetracarboxylic dianhydride glycerol dimethacrylate; adducts of pyromellitic glycerol dimethacrylate and hydroxybutyl (propyl) methacrylate; or the adduct of phthalic anhydride and glycerol dimethacrylate.

3. The cement of claim 2 wherein the carboxylated monomer is pyromellitic glycerol dimethacrylate.

4. The cement of claim 1 wherein the polymerizable base monomer is ethoxylated bis phenol A dimethacrylate; bisphenol A bis(glycidyl methacrylate); or urethane dimethacrylate.

5. The cement of claim 4 wherein the polymerizable base monomer is ethoxylated bis phenol A dimethacrylate.

6. The cement of claim 1 wherein the fluoride source is sodium hexafluorosilicate.

7. The cement of claim 1 wherein paste 1 firther comprises a photoinitiator.

8. The cement of claim 7 wherein the photoinitiator is camphorquinone.

9. The cement of claim 1 wherein paste 1 further comprises a catalyst.

10. The cement of claim 9 wherein the catalyst is benzoyl peroxide.

11. The cement of claim 1 wherein paste 2 further comprises a coinitiator.

12. The cement of claim 11 wherein the coinitiator is a tertiary amine.

13. The cement of claim 12 wherein the tertiary amine is N,N-dimethylaminophenethanol.

14. The cement of claim 1 wherein the pH of the combination after standing for 24 hours is between about 8 and 11.

15. The cement of claim 14 wherein the pH is about 10.

16. The cement of claim 1 wherein the tetracalcium phosphate has a Ca to P mole ratio of 2.05.

17. The cement of claim 1 wherein the tetracalcium phosphate has a Ca to P ratio of 2 or less and wherein CaO has been added to achieve basicity of between about 8 and about 11.

18. The cement of claim 1 wherein paste 1 contains 20 to 60 wt % dicalcium phophate and 10 to 40 wt % carboxylated monomer.

19. The cement of claim 1 wherein paste 2 contains 50 to 90 wt % tetracalcium phophate and 10 to 40 wt % polymerizable base monomer.

20. The cement of claim 1 wherein the combination of paste 1 and paste 2 provides a calcium phosphate concentration of 40 to 80 wt % based on the total combination of paste 1 and paste 2, wherein 60 to 80 wt % is tetracalcium phosphate, and 20 to 40 wt % is dicalcium phosphate.

21. A pulp-capping and base/lining cement comprising the combination of a filler and a liquid comprising a resin system and water, wherein the filler comprises dicalcium phosphate powder, tetracalcium phosphate powder, and a fluoride source; and the resin system comprises a polymerizable monomer and a carboxylated monomer.

22. The cement of claim 21 wherein the carboxylated monomer is pyromellitic glycerol dimethacrylate; 5-(2,5-dioxyl tetrahydrofuranyl)-3-methyl-3-cyclohexene-1,2-dicarboxylic anhydride bis(glycerol dimethacrylate) adduct; biphenyltetracarboxylic dianhydride glycerol dimethacrylate; adducts of pyromellitic glycerol dimethacrylate and hydroxybutyl (propyl) methacrylate; or the adduct of phthalic anhydride and glycerol dimethacrylate.

23. The cement of claim 22 wherein the carboxylated monomer is pyromellitic glycerol dimethacrylate.

24. The cement of claim 21 wherein the polymerizable base monomer is ethoxylated bis phenol A dimethacrylate; bisphenol A bis(glycidyl methacrylate); or urethane dimethacrylate.

25. The cement of claim 22 wherein the polymerizable base monomer is ethoxylated bis phenol A dimethacrylate.

26. The cement of claim 24 wherein the fluoride source is sodium hexafluorosilicate.

27. The cement of claim 21 wherein the pH of the combination after standing for 24 hours is between about 8 and 11.

28. The cement of claim 27 wherein the pH is about 10.

29. The cement of claim 21 wherein the tetracalcium phosphate has a Ca to P mole ratio of 2.05.

30. The cement of claim 21 wherein the tetracalcium phosphate has a Ca to P ratio of 2 or less and wherein CaO has been added to achieve basicity of between about 8 and about 11.

31. The cement of claim 21 wherein the combination of the liquid and the powder provides a calcium phosphate concentration of 40 to 80 wt % based on the total combination, wherein 60 to 80 wt % is tetracalcium phosphate, and 20 to 40 wt % is dicalcium phosphate.

32. A method of dental repair comprising applying an effective amount of a pulp-capping and base/lining cement to damaged pulped region of a tooth, the cement comprising the combination of paste 1 and paste 2, wherein paste 1 comprises a carboxylated monomer, dicalcium phosphate, a fluoride source and water and paste 2 comprises a polymerizable base monomer and tetracalcium phosphate.

33. The method of claim 32 wherein the carboxylated monomer is pyromellitic glycerol dimethacrylate; 5-(2,5-dioxyl tetrahydrofuranyl)-3-methyl-3-cyclohexene-1,2-dicarboxylic anhydride bis(glycerol dimethacrylate) adduct; biphenyltetracarboxylic dianhydride glycerol dimethacrylate; adducts of pyromellitic glycerol dimethacrylate and hydroxybutyl (propyl) methacrylate; or the adduct of phthalic anhydride and glycerol dimethacrylate.

34. The method of claim 33 wherein the carboxylated monomer is pyromellitic glycerol dimethacrylate.

35. The method of claim 32 wherein the polymerizable base monomer is ethoxylated bis phenol A dimethacrylate; bisphenol A bis(glycidyl methacrylate); or urethane dimethacrylate.

36. The method of claim 25 wherein the polymerizable base monomer is ethoxylated bis phenol A dimethacrylate.

37. The method of claim 32 wherein the fluoride source comprises sodium hexafluorosilicate.

38. The method of claim 32 wherein the pH of the combination after standing for 24 hours is between about 8 and 11.

39. The method of claim 32 wherein the tetracalcium phosphate has a Ca to P mole ratio of 2.05.

40. The method of claim 32 wherein paste 1 contains 20 to 60 wt % dicalcium phophate and 10 to 40 wt % carboxylated monomer.

41. The method of claim 32 wherein paste 2 contains 50 to 90 wt % tetracalcium phophate and 10 to 40 wt % polymerizable base monomer.

42. The method of claim 32 wherein the combination of paste 1 and paste 2 provides a calcium phosphate concentration of 40 to 80 wt % based on the total combination, whereby 60 to 80 wt % is tetracalcium phosphate, and 20 to 40 wt % is dicalcium phosphate.

43. A method of dental repair comprising applying an effective amount of a pulp-capping and base/lining cement to damaged pulped region of a tooth, the cement comprising the combination of a filler and a liquid comprising a resin system and water, wherein the filler comprises dicalcium phosphate powder, tetracalcium phosphate powder, and a fluoride source; and the resin system comprises a polymerizable monomer and a carboxylated monomer.

44. The method of claim 43 wherein the carboxylated monomer is pyromellitic glycerol dimethacrylate; 5-(2,5-dioxyl tetrahydrofuranyl)-3-methyl-3-cyclohexene-1,2-dicarboxylic anhydride bis(glycerol dimethacrylate) adduct; biphenyltetracarboxylic dianhydride glycerol dimethacrylate; adducts of pyromellitic glycerol dimethacrylate and hydroxybutyl (propyl) methacrylate; or the adduct of phthalic anhydride and glycerol dimethacrylate.

45. The method of claim 44 wherein the carboxylated monomer is pyromellitic glycerol dimethacrylate.

46. The method of claim 43 wherein the polymerizable base monomer is ethoxylated bis phenol A dimethacrylate; bisphenol A bis(glycidyl methacrylate); or urethane dimethacrylate.

47. The method of claim 44 wherein the polymerizable base monomer is ethoxylated bis phenol A dimethacrylate.

48. The method of claim 32 wherein the fluoride source comprises sodium hexafluorosilicate.

49. The method of claim 32 wherein the pH of the combination after standing for 24 hours is between about 8 and 11.

50. The method of claim 43 wherein the tetracalcium phosphate has a Ca to P mole ratio of 2.05.

* * * * *